US006572823B1

(12) United States Patent
Donahue et al.

(10) Patent No.: US 6,572,823 B1
(45) Date of Patent: Jun. 3, 2003

(54) APPARATUS AND METHOD FOR RECONSTITUTING A SOLUTION

(75) Inventors: John J. Donahue, Haverhill, MA (US); Joseph Haepers, Wilmington, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/458,110

(22) Filed: Dec. 8, 1999

Related U.S. Application Data

(60) Provisional application No. 60/111,552, filed on Dec. 9, 1998.

(51) Int. Cl.[7] .................................... G01N 33/00

(52) U.S. Cl. ............................ 422/63; 422/62; 422/64; 422/68.1; 422/71; 422/81; 422/100; 422/103; 422/104; 436/180; 424/1.85; 600/1; 600/2; 600/3; 600/7; 600/8

(58) Field of Search ............................ 422/62–64, 68.1, 422/71, 81, 100, 103, 104; 424/485; 600/1–3, 7–8; 436/180

(56) References Cited

U.S. PATENT DOCUMENTS 3,847,749 A * 11/1974 Smith et al. ................ 195/127
4,598,049 A * 7/1986 Zelinka et al. .............. 435/287
5,346,999 A * 9/1994 Cathcart et al. ......... 536/25.41
5,425,917 A * 6/1995 Schmid ....................... 422/63
5,559,032 A * 9/1996 Pomeroy et al. ......... 435/289.1
5,695,720 A * 12/1997 Wade et al. .................. 422/82
5,939,330 A * 8/1999 Peterson ..................... 436/180
6,315,979 B1 * 11/2001 Simon et al. ............. 424/1.85

FOREIGN PATENT DOCUMENTS

WO WO-9963547 A2 * 12/1999 ............. G31F/5/00

* cited by examiner

*Primary Examiner*—Jill Warden
*Assistant Examiner*—Kathryn Bex
(74) *Attorney, Agent, or Firm*—Paul D. Golian

(57) ABSTRACT

An apparatus and method are provided for handling a solution. The apparatus comprises a housing and a vial assembly positioned within an enclosure of the housing. The vial assembly maintains at least one vial within the enclosure of the housing. A valve manifold extends within the enclosure of the housing for connection to the vial. A rotation mechanism, also extending within the enclosure of the housing, is operatively connected to the vial assembly for rotating the vial assembly.

14 Claims, 5 Drawing Sheets

APPARATUS AND METHOD FOR RECONSTITUTING A SOLUTION

This application claims the benefit of U.S. Provisional Application No. 60/111,552, filed Dec. 9, 1998.

FIELD OF THE INVENTION

The present invention relates to an apparatus and a method for handling a solution and, in particular, to an apparatus and a method for reconstituting a radioactive solution while ensuring minimal radiation exposure to personnel.

BACKGROUND OF THE INVENTION

New radiopharmaceuticals being developed for diagnostic (e.g., Verluma®) and therapeutic (e.g., $^{166}$Ho-DOTMP and $^{131}$I) purposes often require intricate reconstituting steps before the final drug product is shipped to the end user. For example, to prepare the radiopharmaceutical $^{166}$Ho-DOTMP, a $^{166}$Ho-chloride solution must be quantitatively mixed with the ligand to form the radiopharmaceutical, the pH of the radiopharmaceutical should be tested and adjusted, and the radiopharmaceutical should be sterile filtered into a final dosage vial. Due to the radioactivity associated with the radiopharmaceutical, extreme caution must be used during the mixing and formulation process to minimize the risk of contamination.

The precautions taken to insure the safety of personnel typically involve the use of extensive facilities for handling the reagents and the radiopharmaceutical. The high cost of such facilities has traditionally precluded smaller nuclear medicine clinics and radiopharmacies from being able to reconstitute the radiopharmaceutical at the point of use. Instead, the radiopharmaceutical is reconstituted off-site and transported to the clinic or radiopharmacy where it is to be used. The need to transport the reconstituted radiopharmaceutical introduces an additional safety risk. Further, the delay between the time that the radiopharmaceutical is reconstituted and the time that the radiopharmaceutical is actually used can result in uncertainty with respect to the final dose delivered to the patient receiving the radiopharmaceutical.

In light of the foregoing, it would be highly beneficial to provide an apparatus and a method for reconstituting a radiopharmaceutical wherein the radiopharmaceutical can be reconstituted at the point of use. The apparatus and method should also enable personnel to remotely handle the reagents and the radiopharmaceutical during the mixing and formulation stages of the reconstitution process while shielding the personnel from contamination. Further, the apparatus should be compact so as to be usable as a bench-top model and inexpensive so as to be affordable by clinics and radiopharmacies.

SUMMARY OF THE INVENTION

In accordance with the present invention, an apparatus and a method for handling a solution are provided. The apparatus and method can be used to reconstitute a radiopharmaceutical at the point of use. The apparatus and method also enable personnel to remotely handle the reagents and the radiopharmaceutical during the mixing and formulation stages of the reconstitution process while shielding the personnel from contamination. Further, the apparatus can be made to be compact so as to be usable as a bench-top model and inexpensive so as to be affordable by clinics and radiopharmacies.

The apparatus comprises a housing defining an enclosure designed to shield personnel from hazards associated with the solution. In one embodiment, the housing comprises a radiation shield for shielding personnel from exposure to radiation emitted by reagents contained within the housing. In an alternate embodiment, the housing comprises a shatter-proof and/or flame retardant shield for shielding personnel from the dangers associated with explosive and/or flammable reagents.

A vial assembly is positioned within the enclosure of the housing for maintaining at least one vial within the enclosure of the housing. In one embodiment, the vial assembly defines a vial containment portion integrally formed within the vial assembly for containing said at least one vial. Alternatively, the vial assembly may comprise a vial holder for holding said at least one vial. The vial assembly may further comprise at least one vial shield for positioning over said at least one vial to further protect personnel from hazards associated with the solution. In addition, the vial assembly may comprise a filter, for connection to said at least one vial, to enable gases to escape from the vial while preventing fluid from leaking out of the vial.

A valve manifold extends within the enclosure of the housing for connection to said at least one vial. A syringe is connected to a syringe valve of the valve manifold for injecting and withdrawing fluid through the valve manifold. In one embodiment, a syringe pump is connected to the syringe to facilitate operation of the syringe.

A sampling syringe may be connected between the valve manifold and the vial assembly. In one embodiment, the sampling syringe enables solution to be withdrawn from the apparatus for quality control testing. Alternatively, or additionally, the sampling syringe may enable solution to be withdrawn from the apparatus for measuring and adjusting the pH of the solution.

A rotation means also extends within the enclosure of the housing. The rotation means is operatively connected to the vial assembly for rotating the vial assembly while the vial assembly is connected to the valve manifold.

In one particular embodiment, the apparatus in accordance with the present invention comprises a housing defining an enclosure designed to shield personnel from hazards associated with the solution. A vial assembly is provided within the enclosure of the housing. The vial assembly comprises a combination vial containment portion for containing a combination vial; one or more ligand vial containment portions for containing one or more ligand vials; and a final vial containment portion for containing a final vial. A valve manifold extends within the enclosure of the housing. The valve manifold comprises a sample valve for connection to a sample vial; a combination valve for connection to the combination vial when the combination vial is positioned within the combination vial containment portion; one or more ligand valves for connection to the one or more ligand vials when the ligand vials are positioned within the ligand vial containment portions; and a final valve for connection to the final vial when the final vial is positioned within the final vial containment portion. Rotation means extends within the enclosure to connect to the vial assembly for rotating the vial assembly.

The method for handling a solution in accordance with the present invention comprises the step of injecting a sample solution through a valve manifold into a ligand vial containing a ligand solution, the ligand vial being contained within a vial assembly, the vial assembly being positioned within an enclosure of a housing. Rotation means are then operated, externally from the housing, to rotate the vial assembly and mix the sample solution with the ligand to form a reconstituted sample solution. The pH of the reconstituted sample solution may be determined and adjusted, if the pH is not within an acceptable range. A quality control sample of the reconstituted solution can be taken and analyzed to insure that the reconstituted solution meets predetermined quality control standards. If the reconstituted solution meets the quality control standards, the reconstituted sample solution is transferred to a final vial.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
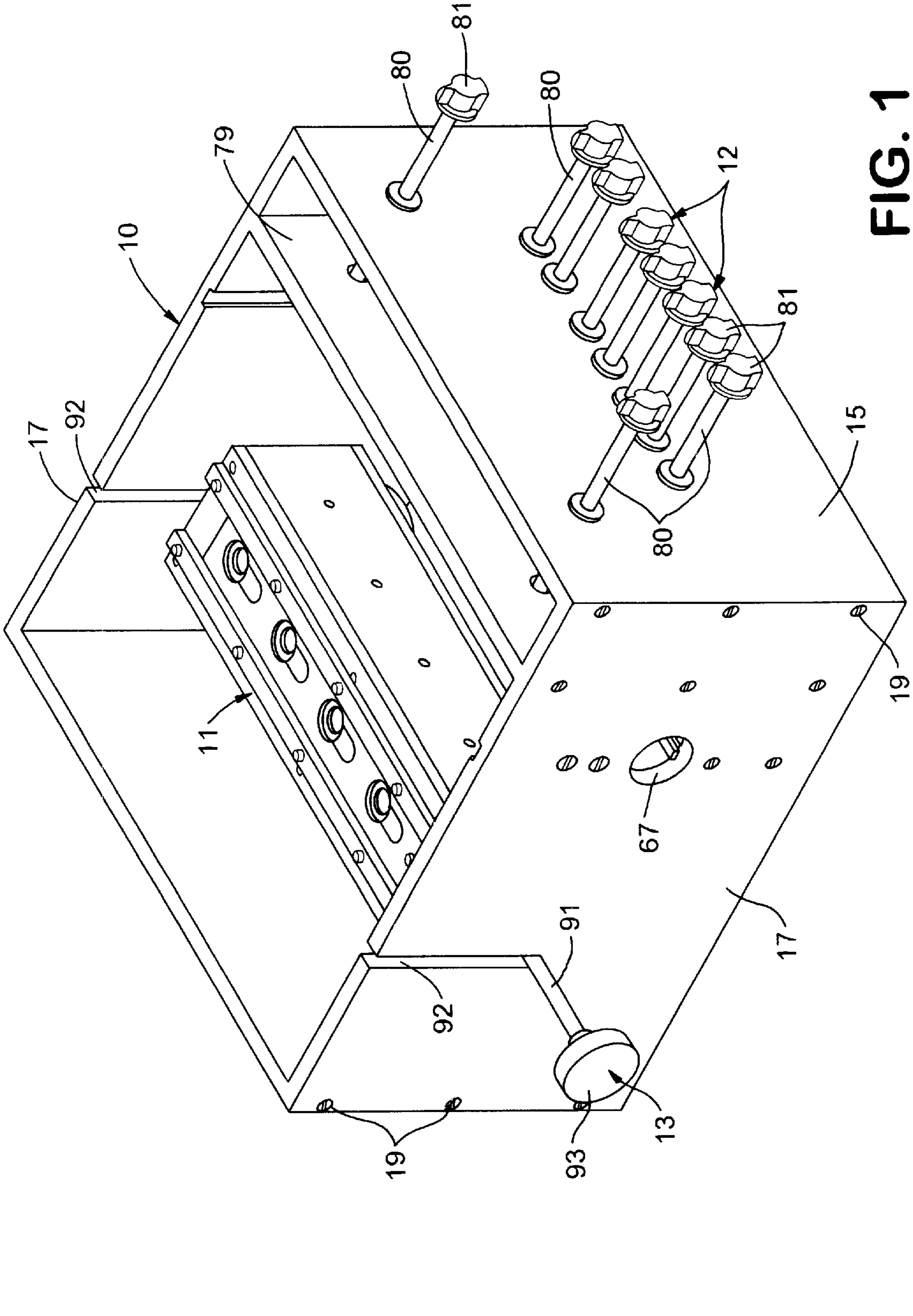
FIG. 1 is a perspective view of an apparatus for reconstituting a radioactive solution in accordance with the present invention shown with a top panel of a housing removed.

An apparatus for reconstituting a sample solution in accordance with the present invention is depicted in FIG. 1. The apparatus comprises a housing 10 which defines an enclosure. A vial assembly 11 is positioned within the enclosure of the housing 10 for maintaining a series of vials within the enclosure. A valve manifold 12 extends within the enclosure for connection to the vials. A rotation device 13 also extends within the enclosure and connects to the vial assembly 11 for rotating the vial assembly 11.

The housing 10 comprises front 15, back, top, bottom, and two side panels 17 assembled to form a receptacle or box. The panels may be manufactured individually and assembled using, for example, screws 19. Alternatively, the panels may be integrally formed. If the apparatus is to be used to reconstitute a radioactive solution, the panels are preferably made from a material effective at absorbing the particular type of radiation emitted by the radioactive solution. For example, the panels may be formed from a methyl acrylate plastic. Alternatively, the apparatus of the present invention can be used to protect personnel from harm when handling explosive or flammable materials and, accordingly, the panels may be formed from a shatterproof and/or fire resistant material.

Figure 2:
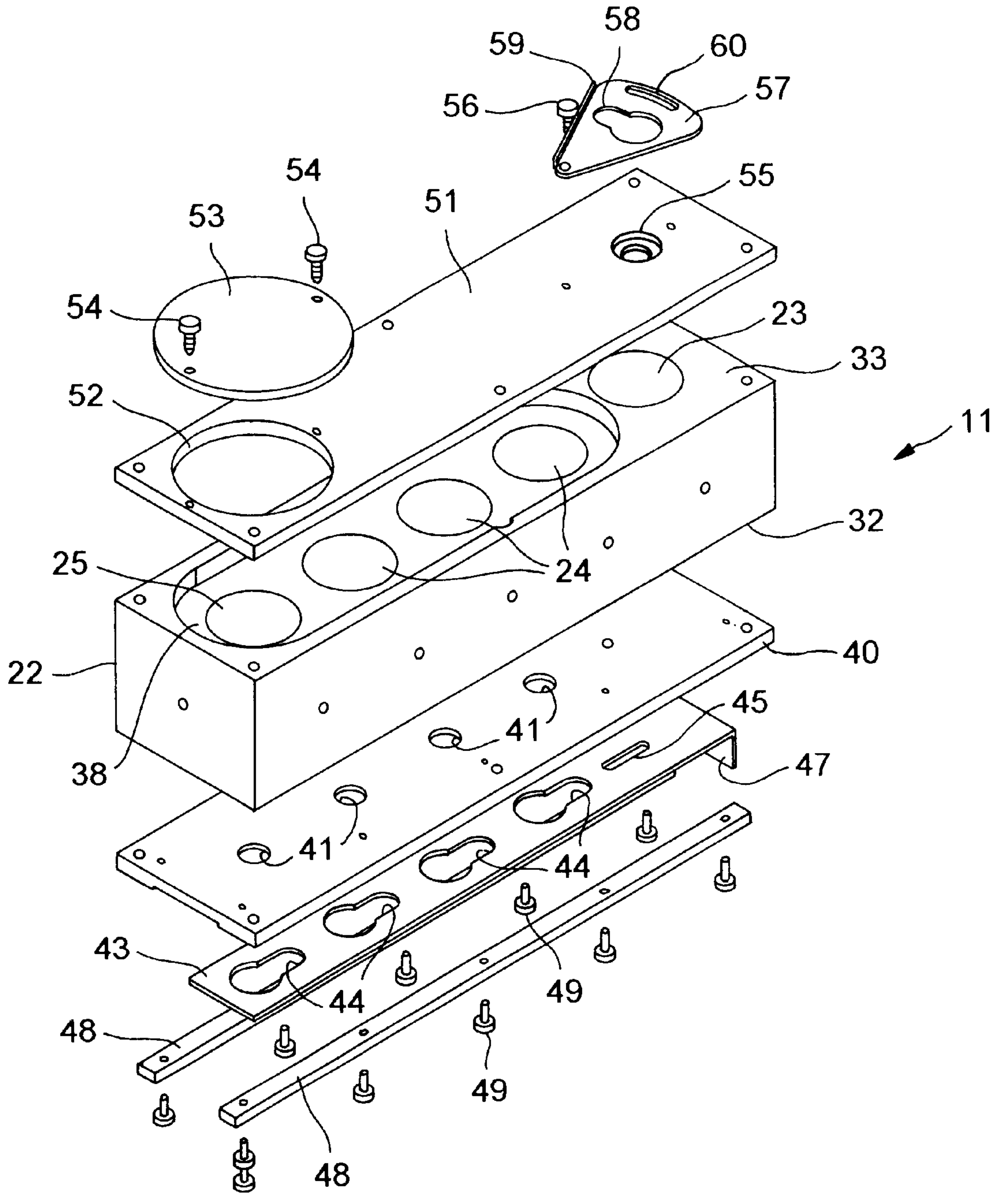
FIG. 2 is an exploded, perspective view of a vial assembly in accordance with the present invention.
Figure 3:
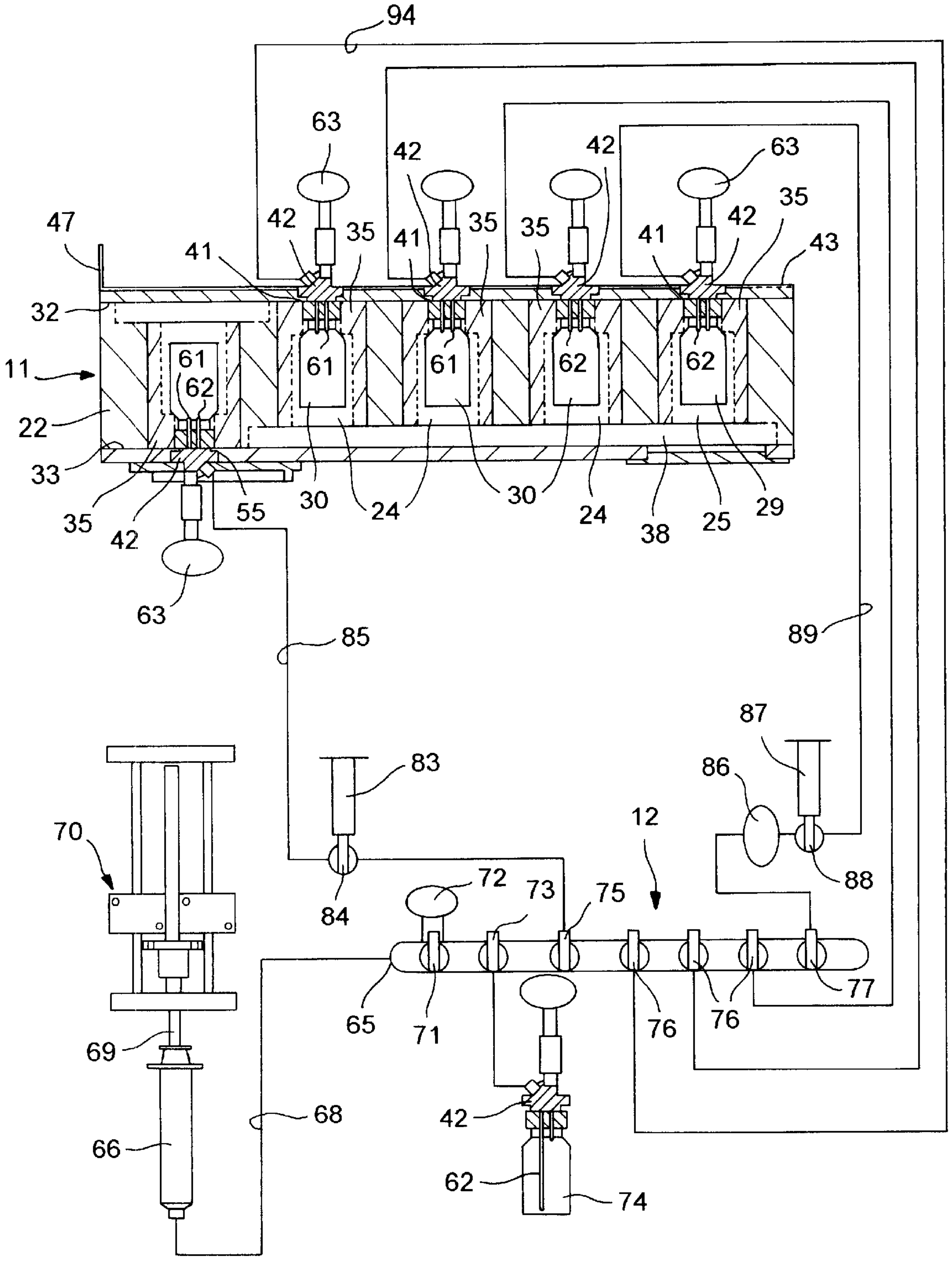
FIG. 3 is a cross-sectional view of the vial assembly depicted in FIG. 2, shown with a combination vial, three ligand vials, and a final vial in place within the vial assembly, and shown connected to a schematic representation of a valve manifold in accordance with the present invention.

The vial assembly 11 is positioned within the enclosure of the housing 10 as shown in FIG. 1. As best seen in FIG. 2, the vial assembly 11 comprises a vial housing 22 defining a combination vial compartment 23, three ligand vial compartments 24, and a final vial compartment 25. However, the preferred number of ligand vial compartments can be increased or decreased, depending upon the number of ligand vials needed for the specific application for which the apparatus is to be used. Specifically, the number of ligand vials must be sufficient to provide the required dose of radiation. As best seen in FIG. 3, each compartment is sized to accommodate a single conventional vial. Specifically, the combination vial compartment 23 and the final vial compartment 25 are designed to hold a combination vial 28 and a final vial 29, respectively. The combination and final vials, 28 and 29 respectively, can be, for example, 30 mL vials sealed with septa and crimps. Each ligand vial compartment 24 is designed to hold a single ligand vial 30, such as a 10 mL vial sealed with septa and crimps and containing a ligand. Each compartment is formed as a generally cylindrical bore extending from a first side 32 to an opposing second side 33 of the vial housing 22.

Figure 4:
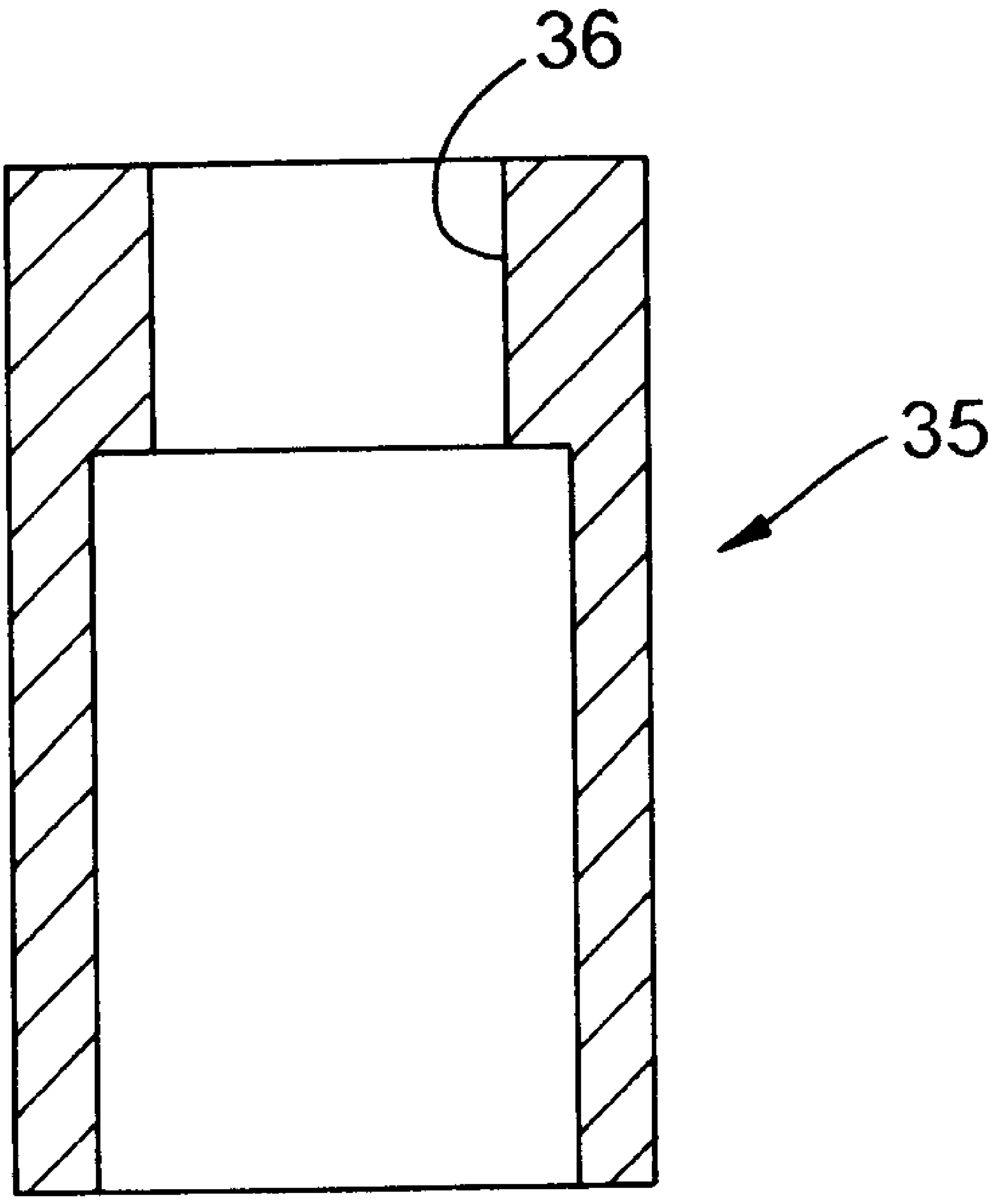
FIG. 4 is a cross-sectional view of a vial shield in accordance with the present invention.

A vial shield or sleeve 35 is positioned within each of the compartments between the vial assembly 11 and each of the combination, final, and ligand vials, 28, 29, and 30 respectively. The vial shields 35 provide further protection from the hazards associated with the solution being handled. Toward that end, when the apparatus is to be used to handle radioactive materials, the vial shields 35 are preferably manufactured from lead. As best seen in FIG. 4, the vial shields 35 are formed as generally cylindrical sections having a longitudinal bore which are designed to slidably fit within the cylindrical bores which form the compartments of the vial housing 22.

Returning to FIG. 3, the combination, final, and ligand vials, 28–30, are positioned within their respective vial compartments in the vial assembly 11. The combination vial 28 is positioned within the combination vial compartment 23 by sliding the combination vial 28, septum first, into the combination vial compartment 23 from the first side 32 toward the second side 33 of the vial housing 22. As shown in FIG. 4, an annular lip 36 along an inside surface of the combination vial shield 35 helps to insure that the combination vial 28 is maintained within the combination vial compartment 23 by providing a snug fit around the septum of the is combination vial 28. Similarly, the ligand vials 30 and the final vial 29 are positioned within the ligand and final vial compartments by sliding the vials, septum first, into their respective vial compartments from the second side 33 toward the first side 32 of the vial housing 22. Accordingly, it will be appreciated that the septum of the combination vial 28 will be adjacent to the second side 33 of the vial housing 22, while the septa of the ligand and final vials, 30 and 29, will be adjacent to the first side 32 of the vial housing 22. The annular lips 36 along inner surfaces of the vial shields 35 help to insure that the ligand and final vials, 30 and 29, are maintained within their respective compartments.

To facilitate insertion of the combination vial 28 within the combination vial compartment 23, a countersink bore 37 is provided along the first side 32 of the vial housing 22 and concentric with the longitudinal bore forming the combination vial compartment 23. Similarly, to facilitate insertion of the ligand and final vials, 30 and 29, within their respective vial compartments, a countersink groove 38 is provided along the second side 33 of the vial housing 22 and encompassing the longitudinal bores forming the ligand and final vial compartments, 24 and 25.

Referring again to FIG. 2, a first cover 40 is positioned to substantially cover the first side 32 of the vial housing 22. The first cover 40 seals the combination vial compartment 23 at the first side 32 of the vial housing 22. Bores 41 are provided within the first cover 40 for gaining access to the septa of the ligand and final vials, 30 and 29. As best seen in FIG. 3, each of the bores 41 is sized and shaped to receive a double needle assembly 42 for puncturing the septa of the ligand and final vials, 30 and 29.

A latching mechanism is provided for securing the double needle assemblies to the ligand and final vials, 30 and 29. As shown in FIG. 2, the latching mechanism comprises a latch plate 43 positioned adjacent to the first cover 40 and slidable between a first and a second position. Access holes 44 are provided in the latch plate 43. When the latch plate 43 is moved to the first position, enlarged sections of the access holes 44 are generally concentric with the ligand and final vial compartments, 24 and 25, thereby enabling the double needle assemblies to be easily connected and disconnected from the ligand and final vials, 30 and 29. When the latch plate 43 is moved to the second position, narrowed sections of the access holes 44 abut the double needle assemblies 42 to prevent the double needle assemblies from being detached from the ligand and final vials, 30 and 29. A slot 45 is provided within the latch plate 43 for receiving the body of a screw (not shown), which can be tightened to secure the latch plate 43 in either the first or the second position. A push plate 47 extends from the latch plate 43 to facilitate movement of the latch plate 43 between the first and second positions. As best shown in FIGS. 1 and 2, slide guides 48 are provided along both long sides of the latch plate 43 to further facilitate sliding of the latch plate 43 between the first and second positions. The slide guides 48 are attached to the first cover 40 by screws 49.

A second cover 51 is provided to substantially cover the second side 33 of the vial housing 22, as shown in FIG. 2. The second cover 51 comprises an access port 52 generally concentric with the final vial compartment 25. A port cover 53 is reversibly attached to the second cover 51 for gaining access to the final vial 29 when the final vial 29 is positioned within the final vial compartment 25. The port cover 53 is attached to the second cover 51 by, for example, screws 54. A bore 55 is provided within the second cover 51 for gaining access to the septum of the combination vial 28. The bore 55 is sized and shaped to receive a double needle assembly 42 for puncturing the septum of the combination vial 28.

A latching mechanism is provided for securing the double needle assembly 42 to the combination vial 28. The latching mechanism comprises a latch plate 57 attached to the second cover 51 by screw 56 and pivotable between a first and a second position. An access hole 58 is provided in the latch plate 57. When the latch plate 57 is rotated to the first position, an enlarged section of the access hole 58 is generally concentric with the combination vial compartment 23, thereby enabling the double needle assembly 42 to be easily connected and disconnected from the combination vial 28. When the latch plate 57 is moved to the second position, a narrowed section of the access hole 58 abuts the double needle assembly 42 to prevent the double needle assembly 42 from being disconnected from the combination vial 28. A push plate 59 extends from the latch plate 57 to facilitate rotation of the latch plate 57 between the first and second positions. A slot 60 is provided within the latch plate 57 for receiving the body of a screw (not shown), which can be tightened to secure the latch plate 57 in either the first or the second position.

As shown in FIG. 3, each of the double needle assemblies 42 comprises two hollow needles, 61 and 62, which extend through the septa of the vials when the double needle assemblies 42 are positioned within the bores, 41 and 55 respectively, of the first and second covers, 40 and 51 respectively. One of the needles 61 extends from within the vial, through the needle assembly 42, and to a hydrophobic filter 63. The hydrophobic filter 63 enables gases to escape from the vial while preventing fluid from passing through the filter 63. The second needle 62 is connected to the valve manifold 12, as described below.

Referring to FIG. 3, the valve manifold 12 comprises an input port 65 for connection to a syringe 66. The syringe 66 is connected to the input port 65 through an access port 67 (see FIG. 1) in one of the side panels 17 of the housing 10 via, for example, Tygon® (Norton Company) tubing 68. As shown, a plunger 69 of the syringe 66 is connected to a syringe pump 70 for accurately controlling the volume of fluid withdrawn or injected by the syringe 66. In one embodiment, the syringe pump 70 is computer controlled to provide the most accurate results.

The valve manifold 12 further comprises a series of two-way valves. A filter valve 71 is connected to a hydrophobic filter 72. The hydrophobic filter 72 is provided to enable gases to be vented from the valve manifold 12 while prohibiting fluid from leaking out of the manifold. A sample valve 73 is provided for connection to one needle 62 of a double needle assembly 42 attached to an isotope supply or sample vial 74. The double needle assembly 42 attached to the sample vial 74 is essentially identical to the double needle assemblies connected to the combination, final, and ligand vials, 28–30. However, the needle 62 of the double needle assembly 42 connected to the sample vial 74 extends substantially toward the bottom of vial 74 to allow fluid to be withdrawn from vial 74 without having to invert vial 74. A combination valve 75 is connected to one of the needles 62 of the double needle assembly 42 attached to the combination vial 28. Three ligand valves 76 are provided with each ligand valve 76 being connected to one of the needles 62 of the double needle assembly 42 attached to each of the ligand vials 30. A final valve 77 is connected to one of the needles 62 of the double needle assembly 42 attached to the final vial 29. Each of the combination, ligand, and final valves, 75–77, are connected to respective needle assemblies 42 via, for example, Tygon® (Norton Company) tubing or some other suitably inert material.

For convenience and as shown in FIG. 1, the valve manifold 12 is attached to an internal panel 79 extending between the two side panels 17 of the housing 10. Accordingly, lead shot or some other radiation adsorbing material can be installed between internal panel 79 and the front is of housing 10 to provide additional radiation shielding. The valve manifold 12, along with its associated tubings and syringes, is assembled into a removable kit to allow for aseptic processing of the entire fluid path. To enable the valves to be opened and closed externally to the housing 10, each valve is connected to an extension rod 80 which extends through the front panel 15 of the housing 10. The extension rods 80 are moveable between a first position wherein the extension rods 80 are connected to the valve manifold 12 and a second position wherein the extension rods 80 are disconnected from the valve manifold 12. Accordingly, when the extension rods 80 are moved to the second position, the valve manifold 12 and its associate tubings and syringes can be removed from the housing 10 for cleaning or replacement. Knobs 81 are attached to the ends of the extension rods 80 which project from the housing 10 to provide leverage for opening and closing the valves and to provide an indication of whether each valve is open or closed.

Returning to FIG. 3, a pH adjustment syringe 83 is connected to a pH sampling valve 84 positioned between the combination valve 75 of the valve manifold 12 and the double needle assembly 42 attached to the combination vial 28. The pH adjustment syringe 83 is provided to enable a sample of fluid to be withdrawn from the line 85 connecting the valve manifold 12 to the combination vial 28. The pH of the withdrawn fluid can then be determined. If the pH of the withdrawn fluid is not within a predetermined range, a buffer solution can be introduced into the combination vial 28 using the pH adjustment syringe 83 in order to modify the pH of the reconstituted solution.

In addition, a sterilizing filter 86 can be connected to the line 89 connecting the valve manifold 12 to the final vial 29. The sterilizing filter 86 is used to sterilize the reconstituted solution prior to injection of the solution into the final vial 29.

A quality control syringe 87 can also be provided for testing the quality of the reconstituted solution. The quality control syringe 87 is connected to a quality control valve 88 positioned between the line 89 connecting the valve manifold 12 to the final vial 29. A sample of the reconstituted solution can be withdrawn, using the syringe 87, from the line 89 connecting the valve manifold 12 to the final vial 29. The withdrawn solution can then be tested to insure that the final reconstituted solution is suitable for its intended use.

The entire vial assembly 11 can be rotated within the housing 10 using the rotation device 13 shown in FIG. 1. Toward that end, the lines connecting the valve manifold to the vial assembly 11 should be of sufficient length to provide slack that allows for rotation of the vial assembly 11. The rotation device 13 enables the vial assembly 11 to be rotated without disturbing the connections between the valve manifold 12 and the combination, ligand, and final vials, 28–30. The rotation device 13 comprises a rotation rod 91 extending from one side of the vial assembly 11 and a collinear rotation rod (not shown) extending from the opposite side of the vial assembly 11. Accordingly, the rotation rods extend through their respective side panels 17 of the housing 10. Toward that end, slots 92 are provided in the side panels 17 of the housing 10 so that when the vial assembly 11 is positioned within the housing 10, the rotation rods sit within the slots 92 and extend from the housing 10. Such an arrangement not only enables the vial assembly 11 to be easily rotated by rotating the rotation rods 91, but also enables the vial assembly 11 to be lifted from the housing 10 for cleaning or replacement. Knobs 93 are provided on the ends of the rotation rods 91 extending from the housing 10 in order to facilitate rotation of the vial assembly 11. A locking pin (not shown) may be provided to prevent the vial assembly 11 from inadvertently rotating.

Figure 5:
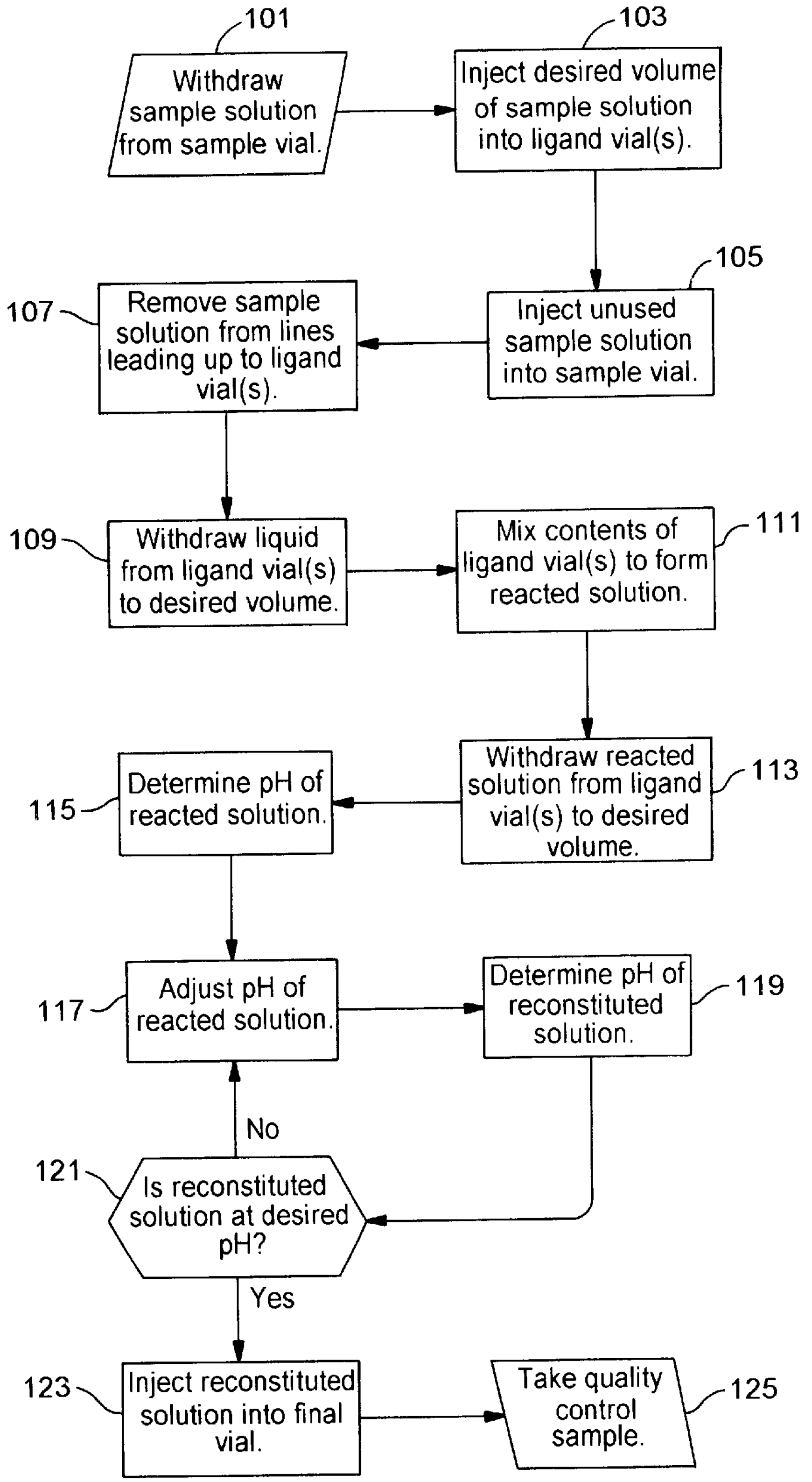
FIG. 5 is a flow chart showing the steps of a method for reconstituting a radioactive solution in accordance with the present invention.

In operation, the apparatus of the present invention is used to reconstitute a solution according to the steps of FIG. 5. A predetermined volume of sample solution is withdrawn from the sample vial 74 at step 101. Toward that end, the sample vial 74 containing the sample solution is connected to the sample valve 73 of the valve manifold 12. The sample valve 73 is then opened to provide fluid contact between the syringe 66 and the sample vial 74. The sample solution is withdrawn from the sample vial 74 by withdrawing the plunger 69 from the syringe 66, either manually or using the syringe pump 70. If more than one sample vial 74 is needed, the syringe 66 is operated to withdraw all of the sample solution from the first sample vial 74, a new sample vial is connected to the sample valve 73 of the valve manifold 12, and the syringe 66 is then operated to withdraw sample solution from the new sample vial.

At step 103, a volume of sample solution is injected into the ligand vials 30 by closing the sample valve 73 and opening the first ligand valve 76 to create a fluid path between the syringe 66 and the first ligand vial 30. The syringe 66 is then operated to fill the line 94 connecting the first ligand vial to the valve manifold 12 with sample solution. The syringe 66 is then used to inject a predetermined volume of sample solution into the first ligand vial 30. The first ligand valve 76 can then be closed. The second and third ligand vials 30 are then filled in an analogous manner.

Any unused sample solution remaining in the syringe 66 is then injected back into the sample vial 74 at step 105. With the ligand valves 76 closed, the sample valve 73 is opened to establish a fluid path between the syringe 66 and the sample vial 74. The syringe 66 is then operated to inject the remaining sample solution back into the sample vial 74.

The lines leading up to the ligand vials 30 are emptied of sample solution at step 107, by closing the sample valve 73 and opening the first ligand valve 76. The syringe 66 is then operated to withdraw any sample solution that remains within the line 94 connecting the valve manifold 12 to the first ligand vial 30. The first ligand valve 76 can then be closed. The lines connecting the valve manifold 12 to the second and third ligand vials 30 are then emptied in an analogous manner. With the ligand valves 76 closed, the sample valve 73 is opened and the syringe 66 is used to inject any solution in the syringe 66 into the sample vial 74.

At step 109, a predetermined amount (e.g., 10 mL) of liquid is withdrawn from the ligand vials 30. The first ligand valve 76 is opened and the predetermined amount of fluid is removed from the first ligand vial 30. The first ligand valve 76 is then closed and the second ligand valve 76 opened. The syringe 66 is then used to withdraw the predetermined amount of fluid from the second ligand vial 30. The second ligand valve 76 is then closed and the third ligand valve 76 opened. The syringe 66 is then used to withdraw the predetermined amount of fluid from the third ligand vial 30. The third ligand valve 76 is then closed and the sample valve 73 opened. The syringe 66 is operated to inject any liquid contained within the syringe 66 into the sample vial 74.

The contents of the ligand vials 30 are then mixed to form a reacted solution at step 111. The mixing is performed by rotating the knobs 93 attached to the rotation rods 91 which extend from the vial assembly 11 to cause the vial assembly 11 to rock back and forth.

At step 113, a volume of reacted solution is withdrawn from the ligand vials 30 by closing the sample valve 73 and opening the first ligand valve 76. A predetermined amount of reacted solution is then removed from the first ligand vial 30 using the syringe 66. The first ligand valve 76 is then closed and the second ligand valve 76 opened. The syringe 66 is then used to withdraw a predetermined amount of reacted solution from the second ligand vial 30. The second ligand valve 76 is then closed and the third ligand valve 76 opened. The syringe 66 is then used to withdraw a predetermined amount of reacted solution from the third ligand vial 30.

At step 115, the pH of the reacted solution is determined. The combination valve 75 is opened to establish a fluid path between the syringe 66 and the combination vial 28. The syringe 66 is then operated to fill the line 85 connecting the combination vial 28 to the valve manifold 12 with reacted solution. The pH sampling valve 84 is then opened to establish a fluid path between the pH adjustment syringe 83 and the line 85 connecting the combination vial 28 to the valve manifold 12. The pH adjustment syringe 83 is then used to withdraw a sample of the reacted solution from the line 85 connecting the valve manifold 12 to the combination vial 28. The pH sampling valve 84 is then closed and the pH adjustment syringe 83 removed from the pH sampling valve 84 so that the pH of the solution within the pH adjustment syringe 83 can be checked.

If the pH of the reacted solution needs to be adjusted, a requisite volume of a buffer solution is added to the combination vial 28 at step 117. Toward that end, the pH adjustment syringe 83 is filled with an appropriate volume of buffer solution. The syringe 83 is then reattached to the pH sampling valve 84 and the valve is opened. The pH adjustment syringe 83 is then operated to inject the buffer solution and any of the reacted solution remaining in the line 85 into the combination vial 28. The contents of the combination vial 28 is then mixed to form the reconstituted solution by rotating the vial assembly 11 as described above.

At step 119, the pH of the reconstituted solution is determined. The vial assembly 11 is rotated so that the first side 32 of the vial housing 22 faces upwardly. The syringe 66 is then used to withdraw a small amount of the reacted solution into the line connecting the valve manifold 12 to the combination vial 28. The pH sampling valve 84 is then opened and the syringe 83 used to withdraw reacted solution from the line 85 connecting the valve manifold 12 to the combination vial 28. The pH sampling valve 84 is then closed, the syringe 83 removed from the pH sampling valve 84, and the pH of the reacted solution determined.

At step 121, it is determined whether the pH of the reconstituted solution is acceptable. If the pH of the reacted solution needs further adjustment, the process returns to step 117. If, however, the pH of the reacted solution is satisfactory, the process proceeds to step 123.

At step 123, the reconstituted solution is removed from the combination vial 28 and the line 85 connecting the valve manifold 12 to the combination vial 28 using the syringe 66 and injected into the final vial 29. The combination valve 75 is closed and the final valve 77 opened to create a fluid path between the valve manifold 12 and the final vial 29. The syringe 66 is then used to inject the reconstituted solution through the sterilizing filter and into the final vial 29.

If a quality control sample is to be obtained at step 125, the quality control valve 88 is opened to create a fluid path between the final vial 29 and the quality control syringe 87. The quality control syringe 87 is then operated to withdraw a sample of the reconstituted solution from the line 89 connecting the valve manifold 12 to the final vial 29. The quality control valve 88 is then closed and any remaining solution contained in the line connecting the valve manifold 12 to the final vial 29 is injected into the final vial 29. The vial assembly 11 can then be rotated so that the second side 33 of the vial housing 22 faces upwardly in order to be able to access and remove the final vial 29 from the vial assembly 11.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for handling a solution comprising:

(a) a housing defining an enclosure;

(b) a vial assembly positioned within the enclosure of the housing and comprising:

(i) a combination vial containment portion for containing a combination vial;

(ii) a ligand vial containment portion or containing a ligand vial; and (iii) a final vial containment portion for containing a final vial;

(c) a valve manifold extending within the enclosure of the housing and comprising:

(i) a sample valve for connection to a sample vial;

(ii) a combination valve for connection to said combination vial when said combination vial is positioned within the combination vial containment portion;

(iii) a ligand valve for connection to said ligand vial when said ligand vial is positioned within the ligand vial containment portion;

(iv) a final valve for connection to said final vial when said final vial is positioned within the final vial containment portion; and (v) a syringe valve for connection to a syringe; and (d) rotation means extending within the enclosure of the housing and operatively connected to the vial assembly for rotating the vial assembly.

2. The apparatus of claim 1 comprising a syringe connected to the syringe valve of the valve manifold.

3. The apparatus of claim 2 comprising a syringe pump connected to the syringe.

4. The apparatus of claim 1 wherein the vial assembly comprises a plurality of ligand vial containment portions.

5. The apparatus of claim 4 wherein the valve assembly comprises a ligand valve for each ligand vial containment portion.

6. An apparatus for handling a solution comprising:

(a) a housing defining an enclosure;

(b) a vial assembly positioned within the enclosure of the housing and comprising:

(i) a combination vial containment portion for containing a combination vial;

(ii) a ligand vial containment portion or containing a ligand vial; and (iii) a final vial containment portion for containing a final vial;

(c) a valve manifold extending within the enclosure of the housing and comprising:

(i) a sample valve for connection to a sample vial;

(ii) a combination valve for connection to said combination vial when said combination vial is positioned within the combination vial containment portion;

(iii) a ligand valve for connection to said ligand vial when said ligand vial is positioned within the ligand vial containment portion; and (iv) a final valve for connection to said final vial when said final vial is positioned within the final vial containment portion;

(d) rotation means extending within the enclosure of the housing and operatively connected to the vial assembly for rotating the vial assembly; and (e) a pH adjustment syringe connected between said combination vial and the combination valve of the valve manifold.

7. The apparatus of claim 6 wherein the vial assembly comprises a plurality of ligand vial containment portions.

8. The apparatus of claim 7 wherein the valve assembly comprises a ligand valve for each ligand vial containment portion.

9. An apparatus for handling a solution comprising:

(a) a housing defining an enclosure;

(b) a vial assembly positioned within the enclosure of the housing and comprising:

(i) a combination vial containment portion for containing a combination vial;

(ii) a ligand vial containment portion or containing a ligand vial; and (iii) a final vial containment portion for containing a final vial;

(c) a valve manifold extending within the enclosure of the housing and comprising:

(i) a sample valve for connection to a sample vial;

(ii) a combination valve for connection to said combination vial when said combination vial is positioned within the combination vial containment portion;

(iii) a ligand valve for connection to said ligand vial when said ligand vial is positioned within the ligand vial containment portion;

(iv) a final valve for connection to said final vial when said final vial is positioned within the final vial containment portion; and (d) rotation means extending within the enclosure of the housing and operatively connected to the vial assembly for rotating the vial assembly; and (e) a quality control syringe connected between said final vial and the final valve of the valve manifold.

10. The apparatus of claim 9 wherein the vial assembly comprises a plurality of ligand vial containment portions.

11. The apparatus of claim 10 wherein the valve assembly comprises a ligand valve for each ligand vial containment portion.

12. An apparatus for handling a solution comprising:

(a) a housing defining an enclosure;

(b) a vial assembly positioned within the enclosure of the housing and comprising:

(i) a combination vial containment portion for containing a combination vial;

(ii) a ligand vial containment portion or containing a ligand vial; and (iii) a final vial containment portion for containing a final vial;

(c) a valve manifold extending within the enclosure of the housing and comprising:

(i) a sample valve for connection to a sample vial;

(ii) a combination valve for connection to said combination vial when said combination vial is positioned within the combination vial containment portion;

(iii) a ligand valve for connection to said ligand vial when said ligand vial is positioned within the ligand vial containment portion;

(iv) a final valve for connection to said final vial when said final vial is positioned within the final vial containment portion; and (d) rotation means extending within the enclosure of the housing and operatively connected to the vial assembly for rotating the vial assembly; and (e) a sterilizing filter connected between said final vial and the final valve of the valve manifold.

13. The apparatus of claim 12 wherein the vial assembly comprises a plurality of ligand vial containment portions.

14. The apparatus of claim 13 wherein the valve assembly comprises a ligand valve for each ligand vial containment portion.

* * * * *